US008557563B2

(12) United States Patent
Zitomer

(10) Patent No.: US 8,557,563 B2
(45) Date of Patent: Oct. 15, 2013

(54) PRESERVATION OF METHANOGENIC, HYDROGEN-UTILIZING MICROBIAL CULTURES

(75) Inventor: Daniel Zitomer, Shorewood, WI (US)

(73) Assignee: Marquette University, Milwaukee, WI (US)

( * ) Notice: Subject to any disclaimer, the term of this patent is extended or adjusted under 35 U.S.C. 154(b) by 71 days.

(21) Appl. No.: 13/079,333

(22) Filed: Apr. 4, 2011

(65) Prior Publication Data

US 2011/0244540 A1 Oct. 6, 2011

Related U.S. Application Data

(60) Provisional application No. 61/341,705, filed on Apr. 2, 2010, provisional application No. 61/396,337, filed on May 26, 2010, provisional application No. 61/396,339, filed on May 26, 2010, provisional application No. 61/396,340, filed on May 26, 2010.

(51) Int. Cl.
*C12N 1/04* (2006.01)
*C12N 1/00* (2006.01)
*C12N 1/20* (2006.01)
*C12P 5/02* (2006.01)
*C12P 1/00* (2006.01)

(52) U.S. Cl.
USPC .......... 435/260; 435/167; 435/41; 435/252.1; 435/243

(58) Field of Classification Search
None
See application file for complete search history.

(56) References Cited

U.S. PATENT DOCUMENTS

| 5,783,081 A | 7/1998 | Gaddy |
| 2009/0107913 A1 | 4/2009 | Johnson |

FOREIGN PATENT DOCUMENTS

| JP | 2003260435 | 9/2003 |
| JP | 2005125149 | 5/2005 |
| KR | 1020060064271 | 6/2006 |
| KR | 1020080089825 | 10/2008 |

OTHER PUBLICATIONS

Kitamura et al. Experimental vacuum spray drying of probiotic foods included with Lactic acid bacteria, Journal of Food Processing and Preservation (2009), 33(6): 714-726.*
Berner et al., "Effect of protective agents on the viability of *Lactococcus lactis* subjected to freeze-thawing and freeze-drying", Scientia Pharmaceutica, 2006, 74:137-149, September.
Bhattad et al., "Culture conditions and cryoprotectant addition influences methanogenic activity after freeze-drying in air", proceedings of International Water Association (IWA) 12th. World Congress on Anaerobic Digestion, Guadalajara, Mexico, Oct. 31-Nov. 4, 1-5., 2010.
Coates et al., "Simple method for the measurement of the hydrogenotrophic methanogenic activity of anaerobic sludges", Journal of Microbiological Methods, 1996, 26:237-246.
Cole et al., "The Ribosomal Database Project (RDP-II) sequences and tools for high-throughput rRNA analysis", Nucleic Acids Research, 2005, 33:D294-D296.
Duran et al., "Bioaugmenting anaerobic digestion of biosolids with selected strains of *Bacillus, Pseudomonas,* and *Actinomycetes* species for increased methanogenesis and odor control", Appl Microbiol Biotechnol, 2006, 73:960-966.
Hubalek, "Protectants used in the cryopreservation of microorganisms", Cryobiology, 2003, 46:205-229.
Schauer-Gimenez et al., "Bioaugmentation for Improved Recovery of Anaerobic Digesters After Toxicant Exposure", Water Research, Jun. 2010, 44(12):1-21.
Tale et al., "Bioaugmentation for Anaerobic Digester Recovery After Organic Overload", Water Environmental Federation Technical Exposition and Conference (WEFTEC 2010), New Orleans, LA, 3936-3947.
Aguilera et al., "Preservation of Biological Materials under Desiccation", Crit Rev Food Sci Nutr. 37(3):287-309.
Castro et al., "Preservation methods for the storage of anaerobic sludges", Biotechnology Letters, 2002, 24:329-333.
Colleran et al., "Use of methanogenic activity tests to characterize anaerobic sludges, screen for anaerobic biodegradability and determine toxicity thresholds against individual anaerobic trophic groups and species", Wat. Sci. Tech., 1992, 25(7):31-40.
Iino et al., "Improvement of the L-drying procedure to keep anaerobic conditions for long-term preservation of methanogens in a culture collection", Microbiol. Cult. Coll., Dec. 2006, 22(2):99-104.
Kolukirik et al., "Changes in acetoclastic methanogenic activity and archaeal composition in a full-scale UASB reactor treating an alcohol distillery effluent", 2004, 10th World Congress on Anaerobic Digestion, 53-58.
Lange et al., "A comprehensive study into the molecular methodology and molecular biology of methanogenic Archaea", FEMS Microbiology Reviews, 2001, 25:553-571.
Malik, "A simplified liquid-drying method for the preservation of microorganisms sensitive to freezing and freeze-drying", Journal of Microbiological Methods, 1990, 12:125-132.
Morgan et al., "Preservation of micro-organisms by drying: A review", Journal of Microbiological Methods, 2006, 66:183-193.
Sakane et al., "Viabilities of dried cultures of various bacteria after preservation for over 20 years and their prediction by the accelerated storage test", Microbiol. Cult. Coll., Jun. 1997, 13(1):1-7.
Saravanane et al., "Bioaugmentation and treatment of cephalexin drug-based pharmaceutical effluent in an upflow anaerobic fluidized bed system", Bioresource Technology, 2001, 76:279-281.
Simione et al., "ATCC preservation methods: freezing and freeze-drying", American Type Culture Collection, Second Edition, 1991.
Staab et al., "Viability of Lyophilized Anaerobes in Two Media", Cryobiology, 1987, 24:174-178.
Tale et al., "Bioaugmentation can improve anaerobic digester performance after organic overload", Proceedings of International Water Association (IWA) 12th. World Congress on Anaerobic Digestion, Guadalajara, Mexico, Oct. 31-Nov. 4, 5, 2010.
International Search Report and Written Opinion for PCT/US2011/031099 dated Dec. 21, 2011.
International Search Report and Written Opinion for PCT/US2011/031077 dated Dec. 22, 2011.

* cited by examiner

*Primary Examiner* — Anand Desai
*Assistant Examiner* — Iqbal H Chowdhury
(74) *Attorney, Agent, or Firm* — Andrus, Sceales, Starke & Sawall, LLP

(57) ABSTRACT

Disclosed are drying methods for preserving cultures of methanogens and dried cultures obtained by the disclosed drying methods. The dried cultures of methanogens may be reconstituted and utilized to bioaugment anaerobic digester systems.

16 Claims, 8 Drawing Sheets

PRESERVATION OF METHANOGENIC, HYDROGEN-UTILIZING MICROBIAL CULTURES

CROSS-REFERENCE TO RELATED APPLICATIONS

The present application claims the benefit under 35 U.S.C. §119(e) to U.S. Provisional Application Nos. 61/341,705, filed on Apr. 2, 2010; 61/396,337, filed on May 26, 2010; 61/396,339, filed on May 26, 2010; and 61/396,340, filed on May 26, 2010; the contents of which are incorporated herein by reference in their entireties

BACKGROUND

The field of the invention relates to preservation methods for bacterial cultures. In particular, the field of the invention relates to preservation methods for methanogenic, hydrogen-utilizing cultures.

Methane is a commercially valuable fuel, as well as synthetic precursor, and can be obtained via microbial fermentation processes. In addition, proper methane production is required for stabilization of municipal, industrial and agricultural wastes via anaerobic digestion. Many euryarchaeotal microorganisms can use hydrogen and carbon dioxide to produce methane. These hydrogenotrophic methanogens are critical to proper functioning of most anaerobic digester systems in which complex substrates are broken down to simpler molecules, such as hydrogen, that are then converted to the final product, methane. If hydrogen utilization slows or stops, the entire biological system can be inhibited or may stop, resulting in an inoperable digester system. In addition, hydrogenotrophs are important in some soil and other environments.

Anaerobic digester systems, agricultural soil, or other environments may be improved if hydrogenotrophs are added. Unfortunately, preserving these organisms can be difficult since they are typically strict anaerobes, and even traces of oxygen are assumed to be toxic to them. In addition, they are thought to be very sensitive to temperatures above about 70 degrees Celcius, and to drying/dessication. On the other hand, it would be beneficial if hydrogenotrophic methanogens could withstand oxygen, and could be heat dried in an air atmosphere and stored in powder or solid form. The powder or solid may also contain protectants and bulking agents. Air drying would potentially be much more economical than freeze drying or other preservation methods. However, the conventional wisdom in the field is that hydrogenotrophs are very sensitive, and would therefore not survive air drying with or without heat in an air atmosphere.

Described herein is a method for preservation of methanogenic cultures, including hydrogenotrophs, by air drying with or without heating. The cultures may be rehydrated with an aqueous solution and utilized to bioaugment anaerobic digester systems to improve production of methane.

SUMMARY

Disclosed herein are methods for preserving methanogens. The methods typically include drying a liquid culture comprising the methanogens to obtain a dried culture comprising the methanogens. Suitable drying methods may include, but are not limited to, air-drying, freeze-drying, heat-drying, and spray-drying.

The liquid cultures utilized in the disclosed methods comprise methanogens and preferably comprise hydrogenotrophic methanogens, but may include methanogens other than hydrogenotrophic methanogens. In some embodiments, the hydrogenotrophic methanogens belong to the order Methanomicrobiales or to the order Methanobacteriales. Suitable hydrogenotrophic methanogens belonging to the order Methanomicrobiales may include *Methanospirillum* spp. such as *Methanospirillum hungatei* or a related hydrogenotrophic methanogen. In some embodiments, *Methanospirillum hungatei* or a related hydrogenotrophic methanogens represent at least about 95% of hydrogenotrophic methanogens belonging to the order Methanomicrobiales in the culture. Other suitable hydrogenotrophic methanogens belonging to the order Methanomicrobiales may include *Methanolinea* spp. such as *Methanolinea tarda* or a related hydrogenotrophic methanogen. Suitable hydrogenotrophic methanogens belonging to the order Methanobacteriales may include *Methanobacterium* spp. such as *Methanobacterium beijingense* or a related hydrogenotrophic methanogen The liquid culture utilized in the disclosed methods may include methanogens other than hydrogenotrophic methanogens, such as acetotrophic methanogens. Suitable acetotrophic methanogens may belong to the order Methanosarcinales.

In the disclosed methods, the liquid culture is dried to reduce the relative moisture content of the liquid culture. Preferably, the dried culture has a relative moisture content of less than about 20% by mass. More preferably, the dried culture has a relative moisture content of less than about 15% by mass.

In the disclosed methods, a cryoprotectant may be added to the liquid culture prior to subjecting the liquid culture to drying. Suitable cryoprotectants may include carbohydrates.

Also disclosed herein are dried cultures comprising methanogens. The dried cultures may be obtained by performing the disclosed methods.

The liquid cultures utilized in the disclosed methods have a specific methanogenic activity. The dried culture may be added to an aqueous solution (i.e., rehydrated) to provide a reconstituted culture having a specific methanogenic activity. Preferably, the reconstituted culture has a specific methanogenic activity that is at least about 50% of the specific methanogenic activity of the liquid culture prior to drying. The reconstituted culture may be utilized to bioaugment an anaerobic digester system, for example, by enhancing methane production of the anaerobic digester system.

DETAILED DESCRIPTION

Figure 1:
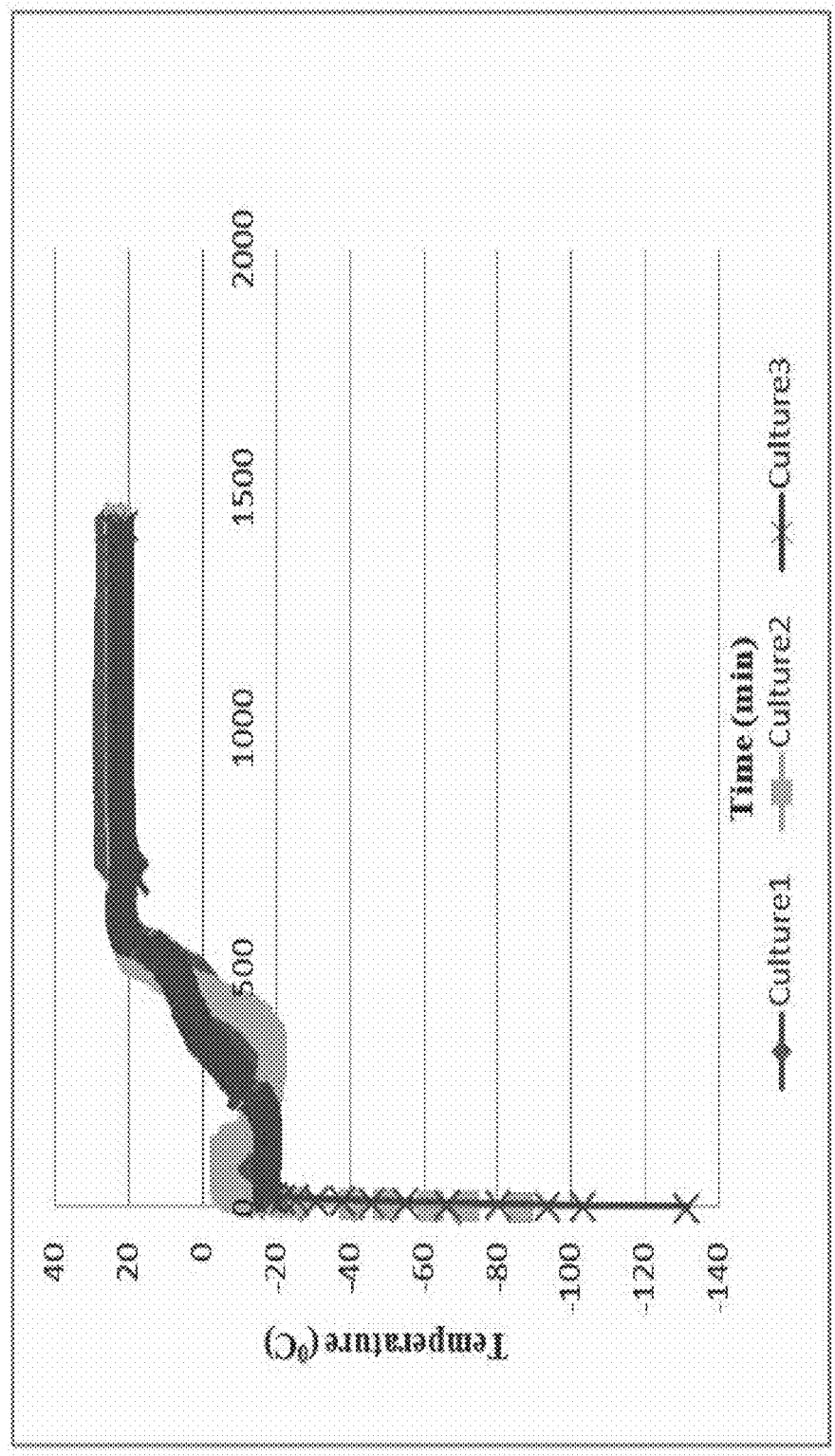
FIG. 1. illustrates freeze-drying behavior of methanogenic cultures.

The disclosed subject matter further may be described utilizing terms as defined below.

Unless otherwise specified or indicated by context, the terms "a", "an", and "the" mean "one or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising."

Dried cultures prepared by the methods disclosed herein may be reconstituted with an aqueous solution and utilized to bioaugment anaerobic digester systems. (See, e.g., Schauer-Gimenez et al., "Bioaugmentation for Improved Recovery of Anaerobic Digesters After Toxicant Exposure," *Wat. Res.* 44 (2010), pp. 3555-3564; Tale et al., "Bioaugmentation Can Improve Anaerobic Digester Performance after Organic Overload," (2010) in proceedings of International Water Association (IWA) 12th. World Congress on Anaerobic Digestion, Guadalajara, Mexico, October 31st-November 4th, 5 pp; and Tale et al., "Bioaugmentation for Anaerobic Digester Recovery After Organic Overload," Water Environment Federation Technical Exposition and Conference (WEFTEC 2010), New Orleans, La., 14 pp); the contents of which are incorporated herein by reference in their entireties). For example, dried cultures prepared by the methods disclosed herein may be reconstituted with an aqueous solution and utilized to improve methane production in anaerobic digester systems. Anaerobic digestion is a series of processes in which microorganisms break down biodegradable material in the absence of oxygen, used for industrial or domestic purposes to manage waste and/or to release energy. The digestion process begins with bacterial hydrolysis of input materials in order to break down insoluble organic polymers such as carbohydrates and proteinaceous material into sugars and amino acids. Acidogenic bacteria then convert the sugars and amino acids into carbon dioxide, hydrogen, ammonia, and organic acids. Acetogenic bacteria then convert these resulting organic acids into acetic acid, and produce additional ammonia, hydrogen, and carbon dioxide. Finally, methanogens convert these products to methane and carbon dioxide.

As used herein, the term "methanogen" is intended to include single celled microorganisms belonging to the domain Archaea such as those Archaea typically present in anaerobic digester systems. Methanogens (or methanogenic Archaea) are responsible for methane production in anaerobic digester systems and include the following genera: *Methanobacterium, Methanobacillus, Methanococcus, Methanosaeta*, and *Methanosarcina*. Microorganisms belonging to these genera may be identified by techniques involving the extraction and analysis of the 16S rRNA gene.

Methanogens utilize a limited number of substrates to generate methane, including carbon dioxide ($CO_2$)-type substrates (e.g., $CO_2$, certain alcohols, formate, pyruvate, and carbon monoxide), methyl substrates (e.g., methanol, methylamine, dimethylamine, trimethylamine, methylmercaptan, and dimethyl sulfide), and acetotrophic substrates (e.g., acetate, pyruvate, and propionate).

In anaerobic digester systems, the two primary substrates that are utilized by methanogens are acetate and hydrogen. Methane ($CH_4$) can be generated in anaerobic digesters through transformation of either acetate or hydrogen by acetotrophic methanogens or hydrogenotrophic methanogens, respectively. Acetotrophic methanogens reduce acetate directly to $CH_4$ and $CO_2$. *Methanosarcina* and *Methanosaeta* (formerly known as *Methanothrix*), both belonging to the order Methanosarcinales, are the only reported acetotrophic methanogens.

The reduction of $CO_2$ using $H_2$ as the electron donor is another method for the generation of $CH_4$ via the equation: $4H_2 + CO_2 \rightarrow CH_4 + 2H_2O$. The majority of the methanogens can utilize $H_2$ and $CO_2$ to produce $CH_4$, including members from the orders Methanobacteriales, Methanococcales, Methanomicrobiales, and Methanopyrales. Some of the genera in the order Methanobacteriales include *Methanobacterium* (e.g., *Methanobacterium beijingense*), *Methanobrevibacter, Methanosphaera, Methanothermus*, and *Methanothermobacter*. Methanococcales are cocci that can be regular or irregular in shape. Genera in this order include *Methanococcus, Methanothermococcus, Methanocaldococcus*, and *Methanotorris*. The order Methanomicrobiales includes a diverse assemblage of methanogens. Genera in this order include *Methanomicrobium, Methanogenium, Methanospirillum* (e.g., *Methanospirillium hungatei*), *Methanoplanus, Methanocorpusculum, Methanoculleus, Methanofollis, Methanolinea* (e.g, *Methanolinea tarda*) and *Methanolacinia*.

The cultures subject to the drying methods contemplated herein may comprise methanogens that are related to the aforementioned methanogens. A methanogen that is related to another methanogen may be defined as a methanogen having a gene which has substantial sequence identity to the corresponding gene in the other methanogen. For example, a methanogen that is related to one of the aforementioned methanogens may have a 16S rRNA gene that exhibits at least about 85%, 90%, 95%, 96%, 97%, 98%, or 99% sequence identity to the 16S rRNA gene of one of the aforementioned methanogens (e.g., as determined by aligning the 16S rRNA genes using the Basic Local Alignment Search Tool (BLAST) available from the National Center for Biotechnology Information (NCBI) at its website). Alternatively, a methanogen that is related to one of the aforementioned methanogens may have an mcrA gene that exhibits at least about 85%, 90%, 95%, 96%, 97%, 98%, or 99% sequence identity to the mcrA gene of one of the aforementioned methanogens. Methyl coenzyme-M reductase (MCR) is the terminal enzyme complex in the biological methane generation pathway and catalyzes the reduction of the methyl group bound to coenzyme-M, thereby releasing methane. This enzyme complex is thought to be unique to and ubiquitous in methanogens which makes it a suitable marker for the detection and characterization of methanogens. The MCR operon exists in two forms, MCRI and MCRII. The MCRI form is thought to be present in all methanogens, while the MCRII form has been found to be present only in the members of the orders Methanobacteriales and Methanococcales. Researchers have selected the mcrA gene, which encodes one protein of the MCRI complex, as a suitable marker for the development of PCR-based detection and characterization of methanogens.

As examples, a methanogen that is related to *Methanospirillum hungatei* may have a 16S rRNA gene or an mcrA gene which has at least about 85%, 90%, 95%, 96%, 97%, 98%, or 99% sequence identity to the corresponding gene in *Methanospirillum hungatei* (i.e., SEQ ID NO:1 and 2, respectively). A methanogen that is related to *Methanolinea tarda* may have a 16S rRNA gene or an mcrA gene which has at least about 85%, 90%, 95%, 96%, 97%, 98%, or 99% sequence identity to the corresponding gene in *Methanolinea tarda* (i.e., SEQ ID NO:3 and 4, respectively). A methanogen that is related to *Methanobacterium beijingense* may have a 16S rRNA gene or an mcrA gene which has at least about 85%, 90%, 95%, 96%, 97%, 98%, or 99% sequence identity to the corresponding gene in *Methanobacterium beijingense* (i.e., SEQ ID NO:5 and 6, respectively).

Cultures subjected to the drying methods contemplated herein may comprise or consist of one or more of the foregoing described methanogens. In some embodiments, cultures subjected to the drying methods contemplated herein comprise a substantially homogenous population of one of the foregoing described methanogens. In other embodiments, cultures subjected to the drying methods contemplated herein comprise a heterogenous population of more than one of the foregoing described methanogens. Contemplated populations of methanogens may be enriched in or depleted of one or more of the foregoing methanogens. For example, in a culture comprising a population of methanogens, one or more of the foregoing methanogens may represent at least about 1%, 2%, 3%, 5%, 10%, 25%, 50%, 75%, 90%, 95%, 96%, 97%, 98%, or 99% of total methanogens in the population. Alternatively, in a culture comprising a population of methanogens, one or more of the foregoing methanogens may represent no more than about 1%, 2%, 3%, 5%, 10%, 25%, 50%, 75%, 90%, 95%, 96%, 97%, 98%, or 99% of total methanogens in the population.

Cultures subjected to the drying methods contemplated herein may be obtained from sources which include, but are not limited to, wastewater treatment plants, for example, biomass obtained from wastewater treatment plants such as sludge. As discussed above, cultures subjected to the drying methods contemplated herein may comprise or consist of a heterogenous population of microorganisms including methanogens. Alternatively, cultures subjected to the drying methods contemplated herein may comprise or consist of a homogenous population of microorganism. Methods of isolating a single microorganism from a heterogenous population of microorganisms are known in the art.

Cultures subjected to the drying methods contemplated herein may be subjected to treatment, selection, or enrichment prior to performing drying. In some embodiments, the cultures are grown in the presence of oxygen prior to drying. For example, the cultures may be grown in the presence of oxygen given at a daily dose of at least about 2.5 mg/L-day (or at a dose of at least about 2.5 mg/L-day, 5 mg/L-day, 10 mg/L-day, 15 mg/L-day, 20 mg/L-day, 25 mg/L-day, 30 mg/L-day, 35 mg/L-day, 40 mg/L-day, 45 mg/L-day, 50 mg/L-day, 55 mg/L-day, 60 mg/L-day, 65 mg/L-day, 70 mg/L-day, 75 mg/L-day, 80 mg/L-day, 85 mg/L-day, 90 mg/L-day, 95 mg/L-day, 100 mg/L-day, 105 mg/L-day, 110 mg/L-day, 115 mg/L-day, 120 mg/L-day, 125 mg/L-day, 130 mg/L-day, 135 mg/L-day, 140 mg/L-day, 145 mg/L-day, 150 mg/L-day, 155 mg/L-day, 160 mg/L-day, 165 mg/L-day, 170 mg/L-day, 175 mg/L-day, 180 mg/L-day, 1.85 mg/L-day, 190 mg/L-day, 195 mg/L-day, 200 mg/L-day, 205 mg/L-day, 210 mg/L-day, 215 mg/L-day, 220 mg/L-day, 225 mg/L-day, 230 mg/L-day, 235 mg/L-day, 240 mg/L-day, 245 mg/L-day, or 250 mg/L-day. The cultures may be grown in the presence of the dose of oxygen for a suitable period of time, such as at least about 1, 2, 3, 4, 5, 6, 7, 8, 9, 10, 15, 20, or 25 days.

In other embodiments, cultures subjected to the drying methods contemplated herein may be grown in the presence of a selected substrate. For example, cultures subjected to the drying methods contemplated herein may be grown in the presence of an organic acid or a salt thereof. Suitable organic acids or salts thereof may include carboxylic acids or salts thereof having at least three carbon atoms. Typically, the carboxylic acids are volatile carboxylic acids. Suitable carboxylic acids or salts thereof may include, but are not limited to propionic acid or propionate salts (e.g., calcium propionate), butyric acid or butyrate salts. For example, cultures subjected to the drying methods contemplated herein may be grown in the presence of an organic acid or a salt thereof given at a daily dose of at least about 0.01 g/L-day (or at a daily dose of at least about 0.02 g/L-day, 0.03 g/L-day, 0.04 g/L-day, 0.05 g/L-day, 0.06 g/L-day, 0.07 g/L-day, 0.08 g/L-day, 0.09 g/L-day, 0.10 g/L-day, 0.11 g/L-day, 0.12 g/L-day, 0.13 g/L-day, 0.14 g/L-day, 0.15 g/L-day, 0.16 g/L-day, 0.17 g/L-day, 0.18 g/L-day, 0.19 g/L-day, 0.20 g/L-day, 0.21 g/L-day, 0.22 g/L-day, 0.23 g/L-day, 0.24 g/L-day, 0.25 g/L-day, 0.30 g/L-day, 0.35 g/L-day, 0.40 g/L-day, 0.45 g/L-day, or 0.50 g/L-day). The cultures may be grown in the presence of the dose of the organic acid or the salt thereof for a suitable period of time, such as at least about 1, 2, 3, 4, 5, 6, 7, 8, 9, 10, 15, 20, or 25 days.

In the presently disclosed methods, a culture comprising one or methanogens is dried by exposure to air, which should be understood to comprise oxygen (e.g., at a concentration of about 21% by volume). In the presently disclosed methods, a culture comprising one or more methanogens is dried to prepare a dry composition having a relatively low moisture content. For example, relative moisture content (RMC) of the dried compositions prepared by the disclosed methods typically are less than about 20%, 15%, 10%, 9%, 8%, 7%, 6%, or 5% by mass.

In the presently disclosed methods, steps for drying a culture comprising one or methanogens may include air-drying (e.g., where the culture is exposed to ambient conditions such as a room temperature of about 15-25° C. (preferably about 20° C.) and standard atmospheric pressure), heat-drying (e.g., where the culture is heated to a temperature of at least about 30° C., 40° C., 50° C., 60° C., 70° C., 80° C., 90° C., 100° C., 110° C., 120° C., 130° C., 200° C., 400° C., 800° C., 1000° C., or 1200° C., or to temperature within a range of about 80-130° C., 90-120° C., or 100-110° C., for example, for a period of time of at least about 10 minutes, 20 minutes, 30 minutes, 45 minutes, 1 hour, 2 hours, 4 hours, 8 hours, 1 day, 2 days, 3 days, 1 week, 2 weeks, or 3 weeks), freeze-drying (e.g., via freezing the culture at a temperature of less than about −20° C., −30° C., −40° C., −50° C., −100° C., or −200° C., subsequently raising the temperature to at least about −10° C., −15° C., −20° C., −25° C., −30° C., −35° C., −40° C., −45° C., −50° C., or −100° C. and subjecting the frozen culture to a vacuum of at least about 1, 2, 3, 4, 5, 10, 15, 20, 25, or 50 pascals, which may be a vacuum sufficient to cause sublimation), or spray-drying. The steps for drying the culture may include a combination of one or more of heating, freezing, and/or exposures to a vacuum as described above.

A cryoprotectant optionally may be added to the liquid cultures prior to being subjected to the disclosed drying methods. Suitable cryoprotectants may include carbohydrates such as sugars (e.g., glucose) and may be added at a suitable concentration to the liquid culture (e.g., to at least about 1%, 2%, 5%, 10%, or 20% by mass). Cryoprotectants are known in the art. (See Morgan et al., 2006; and Hubalek, 2003, the contents of which are incorporated by reference in their entireties).

The cultures subjected to the drying methods contemplated herein may comprise or consist of one or more of the foregoing described methanogens and exhibit specific methanogenic activity (SMA). After the cultures are dried and reconstituted with an aqueous solution, preferably the reconstituted cultures have an SMA (e.g., as measured against $H_2$:$CO_2$) that is at least about 10 ml $CH_4$/hr-g VSS (alternatively reported as $CH_4$/g VSS-h), or more preferably at least about 20, 30, 40, 50, 60, 70, 80, 90, 100, 125, 150, 175, 200, 225, or 250 ml $CH_4$/hr-g VSS. After the cultures are dried and reconstituted with an aqueous solution, preferably the reconstituted cultures have an SMA that is substantially similar to the SMA for the original culture prior to drying. In some embodiments, the reconstituted cultures have an SMA that is at least about 20%, 30%, 40%, 50%, 60%, 70%, 80%, 90%, or 95% of the SMA for the original culture prior to drying.

Illustrative Embodiments

The following embodiments are illustrative and not intended to limit the claimed subject matter.

Embodiment 1

A method for preserving methanogens, the method comprising drying a liquid culture comprising the methanogens by drying the liquid culture to obtain a dried culture comprising the methanogens.

Embodiment 2

The method of embodiment 1, wherein drying is performed by one or more of air-drying, freeze-drying, heat-drying, or spray drying.

Embodiment 3

The method of embodiment 1 or 2, wherein the methanogens comprise hydrogenotrophic methanogens.

Embodiment 4

The method of embodiment 3, wherein the hydrogenotrophic methanogens belong to the order Methanomicrobiales or the order Methanobacteriales.

Embodiment 5

The method of embodiment 4, wherein the hydrogenotrophic methanogens comprise *Methanospirillum hungatei* or a related hydrogenotrophic methanogen.

Embodiment 6

The method of embodiment 5, wherein *Methanospirillum hungatei* or the related hydrogenotrophic methanogen represent at least about 95% of hydrogenotrophic methanogens belonging to the order Methanomicrobiales in the culture (preferably at least about 96%, 97%, 98%, or 99% of hydrogenotrophic methanogens belonging to the order Methanomicrobiales in the culture).

Embodiment 7

The method of any of embodiments 3-6, wherein the hydrogenotrophic methanogens comprises *Methanolinea tarda* or a related hydrogenotrophic methanogen.

Embodiment 8

The method of any of embodiments 3-7, wherein the hydrogenotrophic methanogens comprise *Methanobacterium beijingense* or a related hydrogenotrophic methanogen.

Embodiment 9

The method of any of embodiments 1-8, wherein the methanogens comprise acetotrophic methanogens.

Embodiment 10

The method of embodiment 9, wherein the acetotrophic methanogens belong to the order Methanosarcinales.

Embodiment 11

The method of any of embodiments 1-10, wherein the dried culture has a relative moisture content of less than about 20% by mass (preferably less than about 15%, 10%, 9%, 8%, 7%, 6%, or 5% by mass).

Embodiment 12

The method of any of embodiments 1-11, wherein after the dried culture is reconstituted, the reconstituted culture has a specific methanogenic activity that is at least about 20% of the specific methanogenic activity of the liquid culture prior to drying (preferably at least about 30%, 40%, 50%, 60%, 70%, 80%, 90%, or 95% of the specific methanogenic activity of the liquid culture prior to drying).

Embodiment 13

The method of any of embodiments 1-12, wherein after the dried culture is reconstituted, the reconstituted cultures has a specific methanogenic activity against $H_2$:$CO_2$ that is at least about 10 ml $CH_4$/hr-g VSS (alternatively reported as $CH_4$/g VSS-h), or more preferably at least about 20, 30, 40, 50, 60, 70, 80, 90, 100, 125, 150, 175, 200, 225, or 250 ml $CH_4$/hr-g VSS.

Embodiment 14

The method of embodiment 2, wherein drying comprising heat-drying and the liquid culture is heated to a temperature of at least about 35° C. (preferably to a temperature of at least about 40° C., 40° C., 50° C., 60° C., 70° C., 80° C., 90° C., 100° C., 110° C., 120° C., 130° C., 200° C., 400° C., 800° C., 1000° C., or 1200° C., or to temperature within a range of about 80-130° C., 90-120° C., or 100-110° C.) and preferably for a period of time of at least about 10 minutes, 20 minutes, 30 minutes, 45 minutes, 1 hour, 2 hours, 4 hours, 8 hours, 1 day, 2 days, 3 days, 1 week, 2 weeks, or 3 weeks.

Embodiment 15

The method of embodiment 14, wherein the liquid culture is subjected to a vacuum during the heating (preferably to a vacuum of at least about 1, 2, 3, 4, 5, 10, 15, 20, 25, or 50 pascals).

Embodiment 16

The method of any of embodiments 1-15, comprising adding a cryoprotectant to the liquid culture (e.g., a sugar) to a suitable concentration (e.g., to at least 1%, 2%, 5%, 10%, or 20%) prior to drying the liquid culture.

Embodiment 17

The method of any of embodiments 1-16, wherein prior to drying the liquid culture, the liquid culture was grown in the presence of oxygen (e.g., administered at a dose of at least about 20 mg/L-day for at least about 2 days).

Embodiment 18

The method of any of embodiments 1-17, wherein prior to drying the liquid culture, the liquid culture was grown in the presence of an organic acid or a salt thereof (e.g., propionate administered at a dose of at least about 0.1 g/L-day for at least about 2 days).

Embodiment 19

A dried culture comprising methanogens prepare by any of the methods of embodiments 1-18.

Embodiment 20

A method for bioaugmenting methane production in an anaerobic digester system, the method comprising adding the dried culture of embodiment 18 to the anaerobic digester system.

EXAMPLES

The following examples are illustrative and are not intended to limit the claimed subject matter.

Example 1

Reference is made to Bhattad, U. H., Maki, J. S., Struble, C. A., Schauer-Gimenez, A. E., and Zitomer, D. H., "Culture Conditions and Cryoprotectant Addition Influences Methanogenic Activity After Freeze-Drying in Air," in proceedings of International Water Association (IWA) 12th. World Congress on Anaerobic Digestion, Guadalajara, Mexico, October 31st-November 4th, 5 pp, the content of which is incorporated herein by reference in its entirety.

Abstract

Practitioners often rely on undefined microbial communities that predominate in an anaerobic system. In the near future, however, more methanogenic communities may be customized to fit different applications. Therefore, practical methods to preserve and store customized methanogenic cultures would be helpful. In this study, freeze-drying in air to preserve methanogenic cultures was studied. All cultures were enriched for over one year and received $H_2/CO_2$; one also received air (40 mg $O_2$/L-day), and another received glucose (40 mg/L-day). All cultures maintained 30 to 79% of their original $H_2$-utilizing activity after being freeze dried in air. The culture receiving air during enrichment consistently exhibited higher activity before freeze-drying, after freeze-drying and after being held under conditions simulating 20 years of storage subsequent to freeze-drying. Archaeal clone libraries for each were constructed. The micro-aerobic culture clone library contained a high relative abundance of unstudied phylotypes that could only be classified as archaea; some may represent unique methanogens that are more tolerant of drying and storage in an air atmosphere. Cryoprotectant addition (10% glucose) also resulted in higher activities after freeze drying as well as storage.

Introduction

Methanogenesis requires the presence of specific microbial communities composed of different trophic groups in syntrophic relationships (Speece, 2008). The different communities present in various bioreactors are complex and relatively difficult to define. Therefore, the typical, current engineering approach is to pump waste into a digester and rely on the microorganisms that predominate. However, molecular tools are now being used to identify the organisms involved and understand the link between microbial community structure and digester function or activity (Kolukirik et al., 2004). It is possible that, in the near future, methanogenic microbial communities will be customized for different applications.

In general, methanogens are slow-growing organisms and require significant time to reproduce. Therefore, it would be beneficial if various defined methanogenic cultures could be easily preserved for research and practical applications. Preserved methanogenic cultures could be developed for the following: (1) future research or easy shipment to other laboratories, (2) dissemination and use for standardized tests, such as biochemical methane potential and anaerobic toxicity assays, (3) seeding or re-seeding of laboratory and full-scale reactors, and (4) bioaugmentation of full-scale digesters to increase biogas production and process stability. Bioaugmentation may be an especially beneficial approach to improve anaerobic bioprocesses. Bioaugmentation has been applied to improve the anaerobic degradation rate of difficult-to-degrade compounds such as phenols, cresols, tetrachloroethylene, fat, oil and grease, cattle manure, cellulose and hemicellulose (Schauer-Gimenez et al., 2010). Bioaugmentation has also been used to reduce odor (Duran et al., 2006), shorten the start-up time of new digesters, and decrease the recovery time of organically overloaded reactors (Saravanane et al., 2001), and digesters exposed to a toxicant (Schauer-Gimenez et al., 2010).

The use of wet cultures may be incompatible with some commercial needs. Drying reduces the mass and facilitates less expensive shipping and handling (Aguilera and Karel, 1997). Freezing followed by drying (i.e., freeze-drying) is a preferred technique for preserving and storing microbial cultures in the laboratory as well as in full-scale bio-industries, but "it appears to still be a science based on empirical testing rather than facts and tested theories. The methodologies could be different for different species" (Morgan et al., 2006). Malik (1990) describes several microbial cultures that are sensitive to freezing or freeze-drying including various anaerobes. Major losses in cell viability may occur during each of the three stages of preservation: freezing, drying, and storage.

Culture Freezing.

The process of freezing and, especially, the rate of freezing influence the viability of cells. Freezing can be done either slowly or rapidly. Extra-cellular ice crystal formation, long-term exposure to high solute concentrations, and excessive cell dehydration in slow freezing can contribute to extensive cell damage (Aguilera and Karel, 1997). As Simione and Brown (1991) have written, "[i]n rapid freezing, cell damage may be reduced, and intracellular ice formation is the major contributing factor to cell injury. Rapid freezing in liquid nitrogen is considered to result in less cell damage, but can result in more difficulty during the subsequent drying process." Staab and Ely (1987) employed a shell-freezing method using liquid nitrogen to freeze sensitive anaerobic bacteria including 15 species from the genera *Clostridium, Propionicbacterium, Bifidobacterium, Eubacterium, Bacterioides, Fusobacterium, Peptococcus,* and *Peptostreptococcus*. For this method, the culture was swirled in a flask immersed in liquid nitrogen and the material frozen as a thin shell on the inner surface of the flask. Results showed >50% cell viability after freeze-drying.

Culture Drying.

Drying is used to create stable dried cultures with low residual moisture content (RMC) by removing the moisture from frozen or wet cultures. Low RMC values typically increase survival during storage. Below 10% moisture content, metabolic processes slow or become non-measureable. The lowest practically achievable RMC in the laboratory is between 4 and 7% using freeze-drying (Aguilera and Karel, 1997). Minimum RMC values observed in the laboratory may be impractical on an industrial scale due to scale-up factors and tradeoffs between product yield, stability and cost (Kadam, 1991).

The freeze-drying cycle proceeds in two stages: primary drying and secondary drying. In primary drying, the frozen water is removed by sublimation of ice crystals to water vapor. The major fraction of water is removed during primary drying, but some bound water remains in the dried product. Bound water is trapped within the solid matrix and can take a long time to remove. The bound water is removed during secondary drying at low pressure and low condenser temperature. Secondary drying reduces the RMC and increases the stability of final products (Simione and Brown, 1991). Ideally, the end-point of secondary drying is determined by analysis of the RMC within the freeze-dried products (Morgan et al., 2006). Often, secondary drying is performed for the same length of time as primary drying if the resulting RMC is found to be acceptable (Kadam, 1991).

Culture Storage.

The shelf-life of a freeze-dried culture is highly dependent on the storage temperature and moisture content. Morgan et al., (2006), discussed that storage temperatures of −20° C. and 20° C. cause increased loss of cell viability as compared to 4° C. Sakane and Kuroshima (1997) demonstrated that accelerated storage of liquid-dried bacterial cultures for 2 weeks at 37° C. can simulate 20 years of storage at 5° C. under vacuum.

Cryoprotectants.

The viability of freeze-dried culture can be improved by adding sugars and other carbohydrates as protective agents prior to freezing or drying. The cryoprotectants are viscous and form a glassy state within and around the cell to protect against membrane damage which occurs due to formation of ice crystals during freezing and increases in liquid water solute concentration during freezing and drying (Morgan et al., 2006). An increase in cell viability after freezing and drying depends on the type of protective agent used, and its selection is crucial since some cryoprotectants are toxic to different microbes (Hubalek, 2003).

Preservation of anaerobes using freeze-drying was reported under strict anaerobic conditions, but very limited information regarding methanogenic culture preservation in air exists, possibly due to their high sensitivity to oxygen. The preservation of methanogenic cultures in air would make the process more convenient and economical, but is challenging, and effective preservation and storage methods are needed. In this study, we investigated freeze-drying in an air atmosphere as a method of preservation for three methanogenic cultures. Activity was measured after drying as well as after drying and simulated long-term storage. The effectiveness of enriched culture conditions and cryoprotectant addition was determined.

Materials and Methods

Enrichment Cultures.

Three methanogenic enrichment cultures were developed as described elsewhere (Schauer-Gimenez et al., 2010). Briefly, reactors were seeded with 2 L of anaerobic municipal sludge and operated in daily feed-and-draw mode over two years at 35° C. and a 15-day retention time. All cultures (Culture 1, 2 and 3) received basal nutrient medium (see below) and $H_2:CO_2$ (1:1, v/v ratio) in the headspace every day. In addition, Culture 2 received glucose (40 mg/L-day), whereas Culture 3 received air (40 mg $O_2$/L-day). The mass of $O_2$ theoretically satisfied less than 6% of the oxygen demand. Therefore, the culture dissolved $O_2$ concentration was expected to be negligible. Basal nutrient medium contained the following [mg/L]: $NH_4Cl$ [400]; $MgSO_4.6H_2O$ [250]; $KCl$ [400]; $CaCl_2.2H_2O$ [120]; $(NH_4)_2HPO_4$ [80]; $FeCl_3.6H_2O$ [55]; $CoCl_2.6H_2O$ [10]; $KI$ [10]; yeast extract [100]; the trace metal salts $MnCl_2.4H_2O$, $NH_4VO_3$, $CuCl_2.2H_2O$, $Zn(C_2H_3O_2)_2.2H_2O$, $AlCl_3.6H_2O$, $NaMoO_4.2H_2O$, $H_3BO_3$, $NiCl_2.6H_2O$, $NaWO_4.2H_2O$, and $Na_2SeO_3$) [each at 0.5]; $NaHCO_3$ [5000]; and resazurin [1].

Freezing and Drying.

Waste biomass was collected from all reactors over three days, stored at 4° C. in glass bottles sparged with $N_2:CO_2$ gas (7:3 v/v), then thickened by centrifugation at 4500 rpm for 10 minutes with and without 10% glucose as a cryoprotectant (Colleran et al., 1992). Thickened biomass was transferred to 75 mL freeze-drying flasks (Millrock Technology, Kingston, N.Y., USA) and shell frozen by immersion in liquid nitrogen for approximately 10 minutes (Staab and Ely, 1987). Frozen biomass was then dried using a bench-top freeze dryer (3GenMP Opti-Dry, Millrock Technology, Kingston, N.Y., USA) at a condenser temperature of −45° C. and vacuum of 13.33 pascal (Kadam, 1991). The primary drying time was determined by monitoring flask temperature using a thermocouple (800024, Sper Scientific Ltd., Scottsdale, Ariz., USA). Primary drying was assumed to be complete when the flask temperature increased to the ambient value. Secondary drying was maintained for a time equal to that of primary drying, as recommended elsewhere (Kadam, 1991).

Short-Term and Accelerated Long-Term Culture Storage.

After drying, cultures were analyzed for residual moisture content (RMC) by measuring the total solid (TS), and volatile solids (VS) by standard methods (APHA et al., 1998). Dried cultures were stored in a desiccator containing a $CaCO_3$ dessicant (Drierite®, W. A. Hammond Co., Xenia, Ohio, USA) with an air atmosphere at room temperature for two days before activity testing. Long-term storage was simulated by holding cultures in a similar desiccator with air at an elevated temperature of 35° C. for 15 days, as described by others (Sakane and Kuroshima, 1997); this has been shown to produce activity loss similar to storage for 20 years at 5° C. for many microorganisms.

Specific Methanogenic Activity (SMA) Testing Against $H_2$.

Aliquots of dried cultures were rehydrated in 300 mL of nutrient medium containing L-cysteine hydrochloride (500 mg/L) as a reducing agent. The culture activity against $H_2$ for wet cultures, freeze-dried cultures after drying, and freeze-dried cultures after accelerated storage was determined using the SMA protocol described by Coates et al. (1996) implemented. Serum bottles (160 mL) were charged with 25 mL of biomass suspension (<300 mg/L VSS), sparged with a $H_2:CO_2$ gas mix (4:1 v/v) and sealed with black balch-type rubber septa and aluminum seals. Bottles were pressurized by injecting 100 mL of the $H_2:CO_2$ gas mix (4:1 v/v) and incubated at 35° C. and 150 rpm in an incubator-shaker (model C25KC, New Brunswick Scientific, Edison, N.J., USA). The volume of gas remaining was measured over time with a glass syringe and water-lubricated glass plunger. After measurement, gas was re-injected into the serum bottle.

The gas volume decrease was calculated from the initial gas volume in test bottles (100 mL) less the gas volume remaining at a given time. The $H_2:CO_2$ gas utilized was calculated as the gas volume decrease less the endogenous control bottle gas volume produced. Methane production was calculated as the volume of $H_2:CO_2$ gas utilized divided by the stoichiometric ratio 4 (i.e., 4 moles of $H_2$ and 1 mole of $CO_2$ produce 1 mole of $CH_4$). Maximum methane production rate (mL $CH_4$/h) was determined by linear regression using the initial points on a graph of cumulative methane produced versus time. SMA (mL $CH_4$/g of VSS-h) was calculated by dividing the maximum methane production rate by the system VSS mass measured by standard methods (APHA et al., 1998). SMA testing, endogenous controls and abiotic controls were run in triplicate. Gas leakage in abiotic controls was negligible throughout the analyses. A one sided Student's t-test with unequal population variance was used to compare activity data.

Archaeal Community Analysis.

Archaeal communities were analyzed by building clone libraries for a fragment of the 16S rRNA gene using ArchF (5'-TTCCGGTTGATCCYGCCGGA-3' (SEQ ID NO:7)) and ArchR (5'-YCCGGCGTTGAMTCCAATT-3' (SEQ ID NO:8)) primers as described elsewhere (Schauer-Gimenez et al., 2010). DNA was extracted using the PowerSoil DNA Isolation Sample Kit (MoBio Laboratories, Inc., Carlsbad, Calif., USA) and PCR amplified using EconoTaq® PLUS 2× Master Mix (Lucigen Corp., Middleton, Wis., USA). PCR products were cloned using a TOPO TA Cloning® Kit (Invitrogen, Carlsbad, Calif., USA). Transformants were selected by blue-white screening, and direct colony PCR was performed on white colonies. PCR products were cleaned, concentrated, and processed using an UltraClean™ Clean-Up Kit (MoBio Laboratories, Carlsbad, Calif., USA) prior to sequencing at an outside facility (University of Chicago Cancer Research Center). Consensus sequences were assembled, and vector sequences as well as chimeras were removed as described elsewhere (Schauer-Gimenez et al., 2010). The Basic Local Alignment Search Tool (BLAST) was used to identify similar sequences. The SeqMatch program on the Ribosomal Database Project (RDP) website was used to identify taxonomic classifications (Cole et al., 2007).

Results and Discussion

All three methanogenic cultures maintained $H_2$-utilizing activity after being freeze dried and stored in an air atmosphere. The drying behaviors of all cultures were similar. After 12 h, the drying flask reached the ambient temperature and primary drying was completed (See FIG. 1). Secondary drying was then continued for an additional 12 h to remove bound water and obtain a stable product. The RMC of freeze-dried cultures was between 9 and 13% by mass.

Culture conditions influenced the microbial community structure as well as activities observed before freeze drying, after freeze drying, and after storage. Cultures 1 and 3 consistently demonstrated significantly higher activity (p<0.005) as compared to Culture 2 (See FIGS. 2 and 3). The glucose addition to Culture 2 may have increased the VSS mass associated with fermentative bacteria and acetoclastic methanogens, thus decreasing the $H_2$-utilizing fraction of the total VSS. Therefore, the hydrogenotrophic methanogens may have comprised a lower fraction of the total biomass in Culture 2 and the activity against $H_2$ was lower. This is supported by archaeal community analysis. The relative abundance of sequences related to known hydrogenotrophic methanogens was lower in Culture 2, whereas the relative abundance of sequences related to known acetoclastic methanogens was higher in Culture 2 (See FIG. 4).

Figure 2:
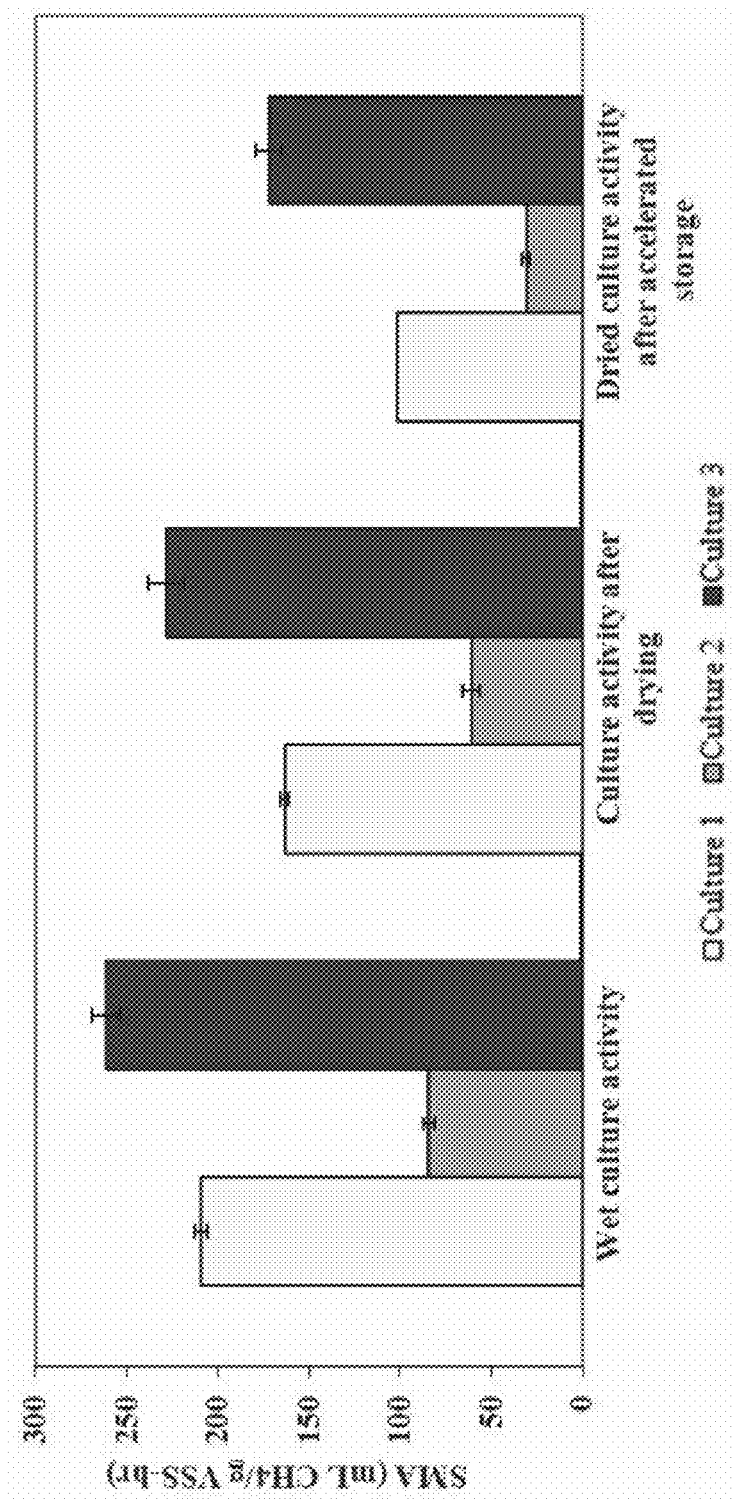
FIG. 2. illustrates methanogenic activity of cultures with cryoprotectant. Error bars represent standard deviation among three replicates.
Figure 3:
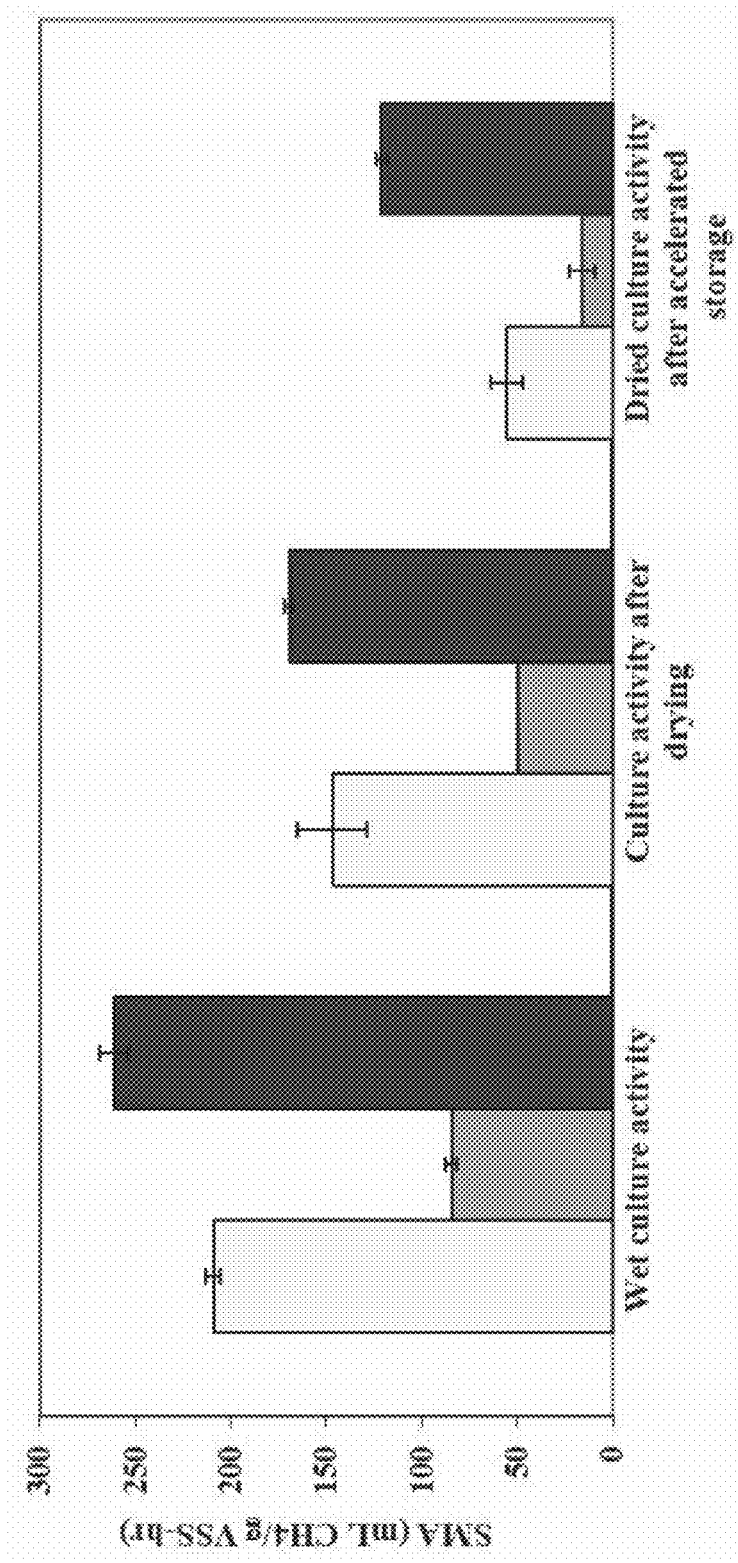
FIG. 3. illustrates methanogenic activity of cultures without cryoprotectant. Error bars represent standard deviation among three replicates FIG. 4. illustrates percent Archaeal population based on total sequences FIG. 5. illustrates percent activity of freeze-dried cultures with and without addition of cryoprotectant with respect to wet cultures. Error bars represent standard deviation among three replicates.
Figure 4:
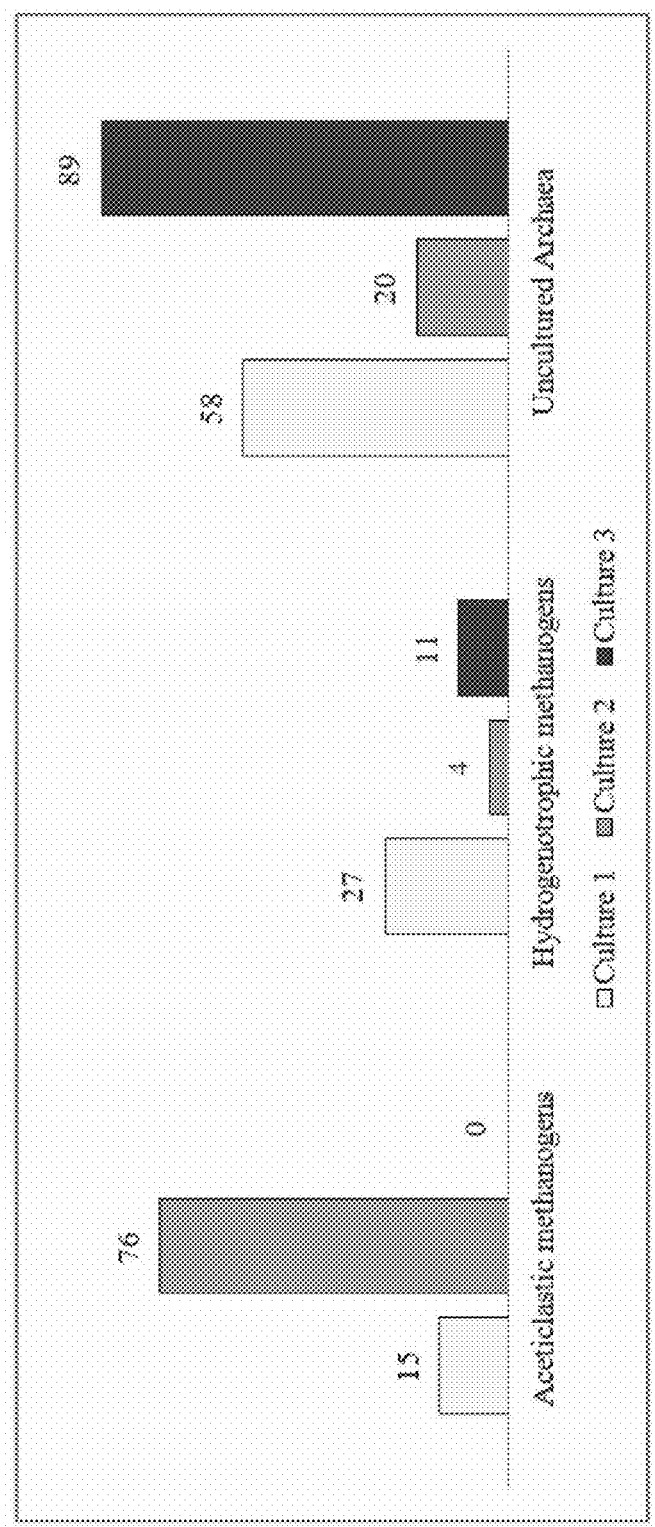

The culture 3 which was enriched with a low daily dose of air (i.e., $O_2$) consistently exhibited higher activity before freeze-drying, after freeze-drying, and after storage following freeze-drying (See FIGS. 2 and 3). Addition of small amount of air shifted the archeal community, causing a higher relative abundance of archaeal phylotypes of unknown phyla (See FIG. 4). The unstudied archaeal phylotypes may be more tolerant of drying and storage in an air atmosphere and may be methanogens. Air addition also resulted in a decrease in the relative abundance of phylotypes closely related to known aceticlastic methanogens (See FIG. 4).

Figure 5:
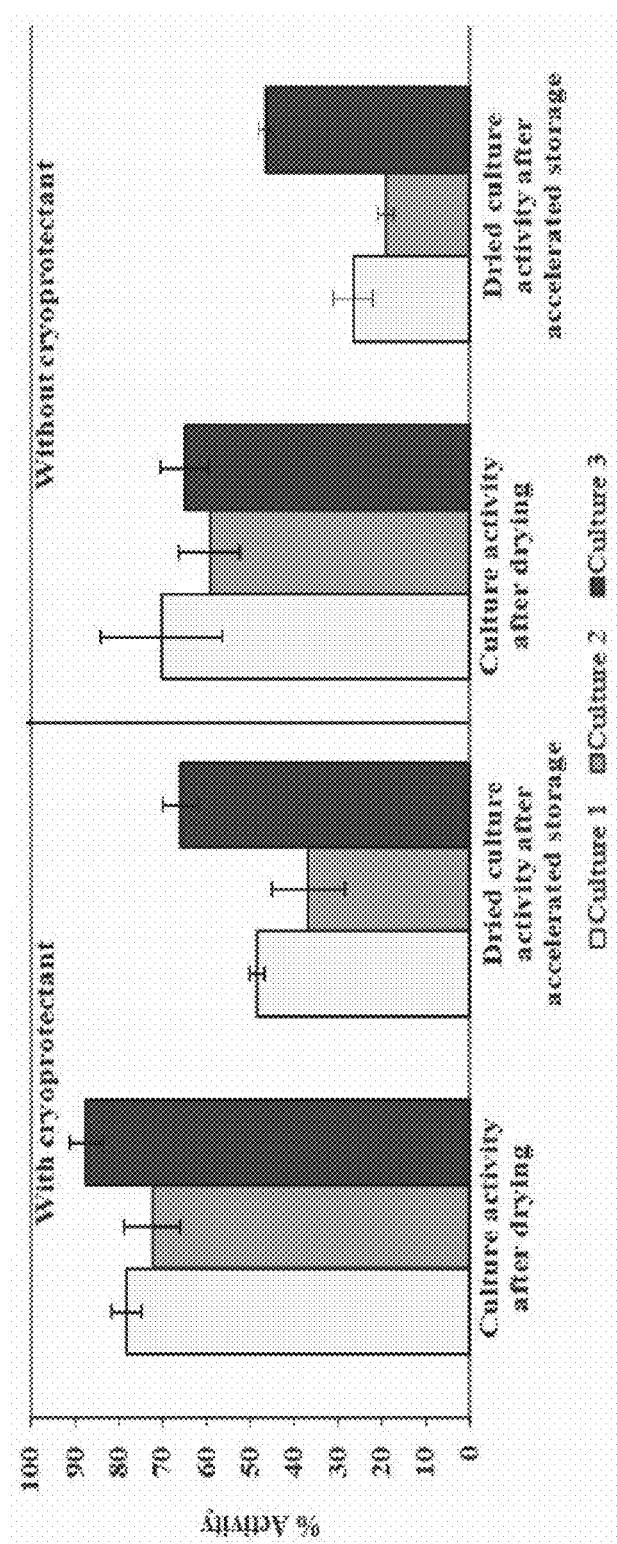

Cryoprotectant addition resulted in higher methanogenic activity after both freeze-drying and storage. The beneficial influence of cryoprotectant addition was more pronounced after accelerated storage than it was after drying (See FIG. 5). The percent activity preserved was calculated as the activity value after freeze-drying or storage divided by the activity value before freeze drying multiplied by 100. The average percent activity preserved after freeze-drying for all cultures was 79% with cryoprotectant and 65% without cryoprotectant, whereas the average percent activity preserved after freeze-drying and subsequent accelerated storage was 50% with cryoprotectant and 30% without cryoprotectant respectively (See FIG. 5). Similar results were discussed by Colleran et al. (1992) for cultures dried and stored under anaerobic conditions. They showed that addition of 10% glucose during freeze-drying resulted in 32% higher activity of granular anaerobic sludge immediately after drying and 48.5% after freeze-drying with seven months of subsequent storage under anaerobic conditions. Berner and Viernstein (2006) demonstrated that 40% of the original viability of a freeze-dried *Lactococcus lactis* strain cultivated under anaerobic conditions at 30° C. was preserved when 15% sucrose was used as a cryoprotectant, but no colony forming units (CFUs) were detected when the cryoprotectant was not added.

Conclusions

Methanogenic activity can be preserved after freeze-drying and storage of active cultures in an air atmosphere. Growth conditions before freeze-drying influenced the hydrogenotrophic activity after freeze-drying. In this regard, methanogenic cultures grown in the presence of air maintained more methanogenic activity after freeze-drying in air as compared to strictly anaerobic cultures. Clone libraries constructed from micro-aerobic methanogenic cultures contained unstudied phylotypes that could only be classified under the domain Archaea (i.e, they could not be resolved to the phylum level). Some of these unstudied archaea may have been unique methanogens that were more tolerant of drying and storage in an air atmosphere; however, additional research is required to confirm this hypothesis. Adding 10% glucose as a cryoprotectant resulted in increased methanogenic activity after freeze drying and after storage of the freeze-dried product. In addition, micro-aerobic culture conditions and glucose addition as a cryoprotectant are practical methods to increase hydrogenotrophic methanogenic activity after freeze-drying in air.

REFERENCES FOR EXAMPLE 1

Aguilera J., Karel M. (1997). Preservation of biological materials under desiccation. *Crit Rev Food Sci Nutr* 37(3), 287-309.

APHA (American Public Health Association), AWWA (American Waterworks Association), and WEF (Water Environment Federation) (1998). *Standard Methods for the Examination of Water and Wastewater*, 20th edition.

Berner D., Viernstein H. (2006). Effect of protective agents on the viability of *Lactococcus lactis* subjected to freeze-thawing and freeze-drying. *Scientia Pharmaceutica (Sci. Pharm.)*. 74, 137-149.

Coates J. D., Coughlan M. F. and Colleran E. (1996). Simple method for the measurement of the hydrogenotrophic methanogenic activity of anaerobic sludges. *J Microbial Methods*. 26(3), 237-246.

Cole J., Chai B., Farris K, Wang Q., Kulam S., McGarrell D., Garrity G. and Tiedje J. (2005). The Ribosomal Database Project (RDP-II): sequences and tools for high-throughput rRNA analysis. *Nucleic Acids Res.* 33(Database Issue), D294.

Colleran E., Concannon F., Golden T., Geoghegan F., Crumlish B., Killilea E., Henry M. and Coates J. (1992). Use of methanogenic activity tests to characterize anaerobic sludges, screen for anaerobic biodegradability and determine toxicity thresholds against individual anaerobic trophic groups and species. *Water Science & Technology [WATER SCI.TECHNOL.]*. 25(7).

Duran M., Tepe N., Yurtsever D., Punzi V. L., Bruno C. and Mehta R. J. (2006). Bioaugmenting anaerobic digestion of biosolids with selected strains of Bacillus, Pseudomonas, and Actinomycetes species for increased methanogenesis and odor control. *Appl Microbial Biotechnol*. 73(4), 960-966.

Hubalek Z. (2003). Protectants used in the cryopreservation of microorganisms* L *Cryobiology*. 46(3), 205-229.

Kadam K. L. (1990). Granulation technology for bioproducts. Informa Healthcare., Dated, May 14, 2010.

Kolukirik M., Ince O. and Ince B. (2004). Changes in acetoclastic methanogenic activity and archaeal composition in a full-scale UASB reactor treating an alcohol distillery effluent, 53-58.

Lange and Ahring (2001). A comprehensive study into the molecular methodology and molecular biology of methanogenic Archaea." *FEMS Microbiology Reviews*. 25: 553-571.

Malik K. A. (1990). A simplified liquid-drying method for the preservation of microorganisms sensitive to freezing and freeze-drying. *J. Microbiol Methods*. 12(2), 125-132.

Morgan C., Herman N., White P. and Vesey G. (2006). Preservation of micro-organisms by drying; A review. *J Microbiol Methods*. 66(2), 183-193.

Sakane T., Kuroshima K. (1997). Viabilities of dried cultures of various bacteria after preservation for over 20 years and their prediction by the accelerated storage test. *Microbiol. Cult. Coll.* 13, 1-7.

Saravanane R., Murthy D. and Krishnaiah K. (2001). Bioaugmentation and treatment of cephalexin drug-based pharmaceutical effluent in an upflow anaerobic fluidized bed system. *Bioresour rechnol*. 76(3), 279-281.

Schauer-Gimenez A. E., Zitomer D. H., Maki J. S, and Struble C. A. (2010). Bioaugmentation for Improved Recovery of Anaerobic Digesters After Toxicant Exposure. *Water Res.*

Simione F. P., Brown E. M. (1991). ATCC preservation methods: freezing and freeze-drying. American Type Culture Collection, Dated, May 14, 2010.

Speece R. E. (2008). *Anaerobic Biotechnology and Odor/Corrosion Control for Municipalities and Industries*. Archae Press, Nashville Tenn.

Staab J. A., Ely J. K. (1987). Viability of lyophilized anaerobes in two media. *Cryobiology*. 24(2), 174-178.

Example 2

The following example relates to air-drying of methanogenic enrichment cultures at elevated temperatures.

Materials and Methods

Enrichment Cultures.

Two methanogenic enrichment cultures were used as described elsewhere (Schauer-Gimenez et al., 2010) to perform air drying. The culture 1 was enriched with $H_2/CO_2$ (1:1 v/v) under strict anaerobic conditions whereas culture 2 was enriched with $H_2/CO_2$ (1:1 v/v) and low dose of $O_2$ in the form of air.

Air-Drying of Cultures.

Waste biomass was collected from these reactors over three days, stored at 4° C. in glass bottles sparged with $N_2:CO_2$ gas (7:3 v/v), then thickened by centrifugation at 4500 rpm for 10 minutes with and without 10% glucose as a cryoprotectant (Colleran et al., 1992). The thickened biomass suspension (20 mL) was transferred to a 25-mL ceramic crucible. The biomass was air-dried by placing a crucible in a 104° C. oven for 10 to 12 hrs.

Short-Term and Simulated Long-Term Culture Storage.

After drying, cultures were analyzed for residual moisture content (RMC) by measuring the total solid (TS), and volatile solids (VS) by standard methods (APHA et al., 1998). Dried cultures were stored in a desiccator in air at room temperature for two days before activity testing. Long-term storage was simulated by holding cultures in a similar desiccator in air at an elevated temperature of 35° C. for 15 days, as described by others (Sakane and Kuroshima, 1997); this has been shown to produce activity loss similar to storage for 20 years at 5° C. under vacuum for many microorganisms.

Specific Methanogenic Activity (SMA) Testing Against $H_2$.

The activity of cultures against $H_2$, after air drying as well as air drying and simulated storage was determined using the SMA protocol described by Coates et al. (1996) and the results were compared with wet cultures (controls). Briefly, aliquots of dried cultures were rehydrated in 300 mL of nutrient medium containing L-cysteine hydrochloride (500 mg/L) as a reducing agent. The activity test was performed in 160-mL serum bottles by injecting 100 mL pressurized gas mixture of $H_2:CO_2$ (4:1 v/v) in 25-mL biomass suspension (<300 mg/L VSS), incubated at 35° C. and 150 rpm. SMA (mL $CH_4$/g of VSS-h) was calculated by dividing the maximum methane production rate by the system volatile suspended solids (VSS) mass measured by standard methods (APHA et al., 1998).

Results

Figure 6:
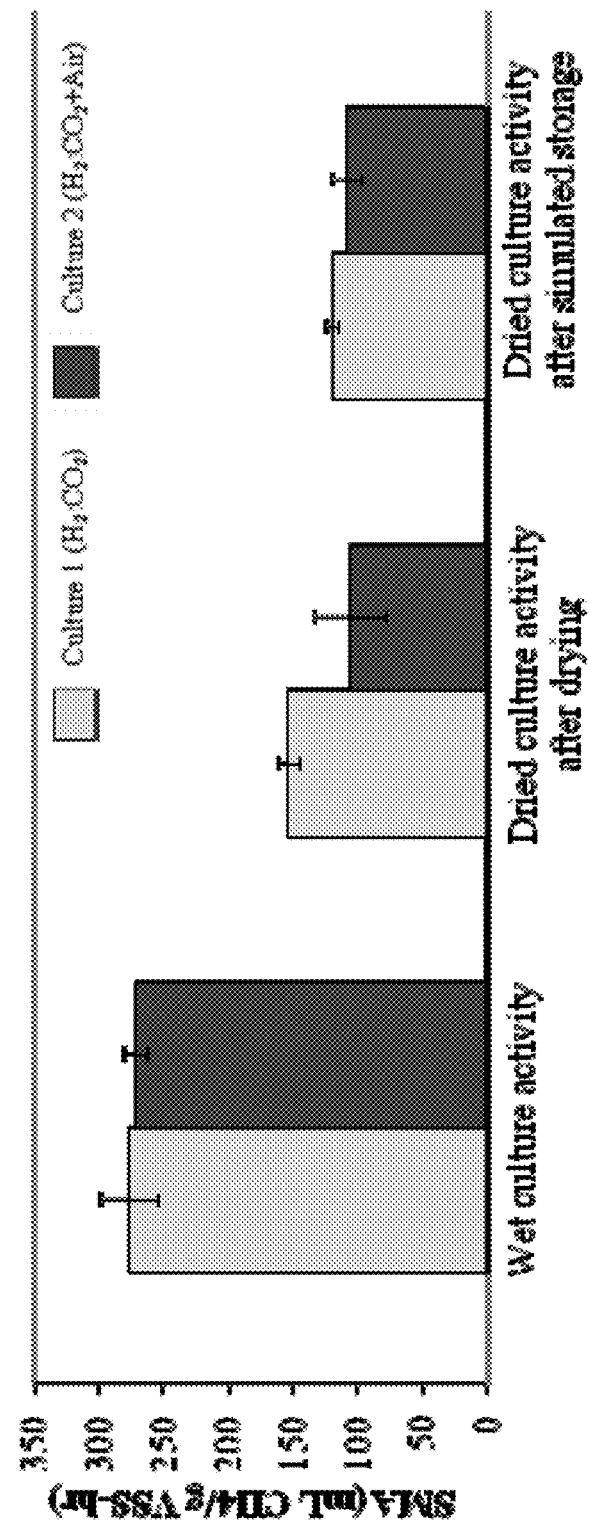
FIG. 6 illustrates methanogenic activity of cultures with protective agent. Error bars represent standard deviation among three replicates.
Figure 7:
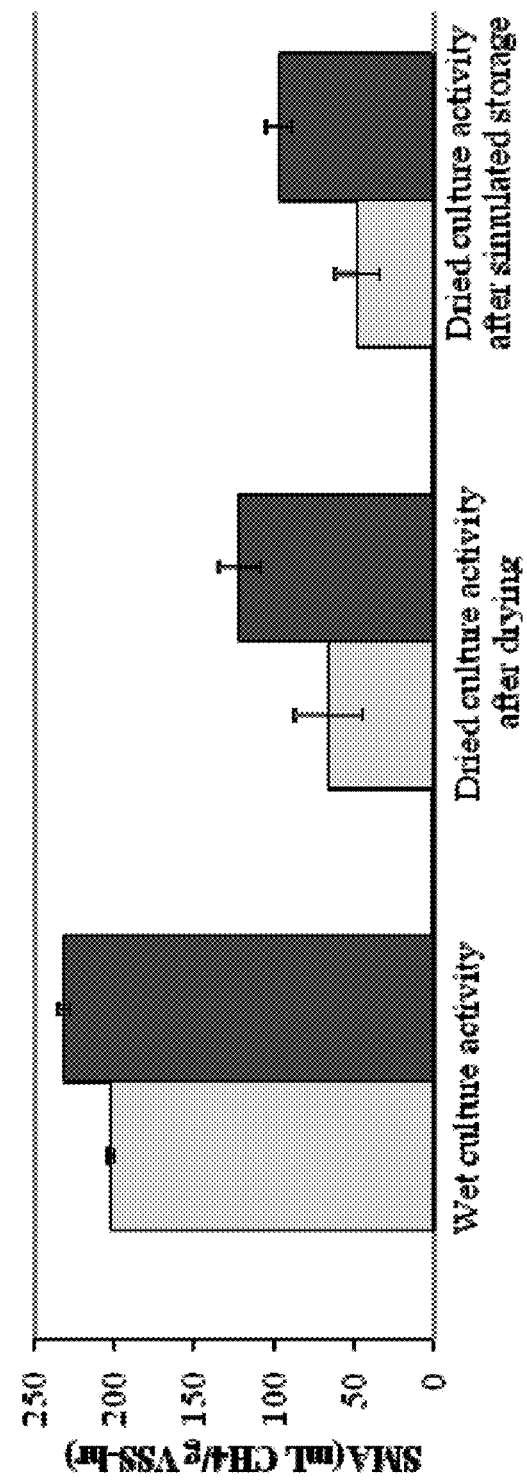
FIG. 7 illustrates methanogenic activity of cultures without protective agent. Error bars represent standard deviation among three replicates.
Figure 8:
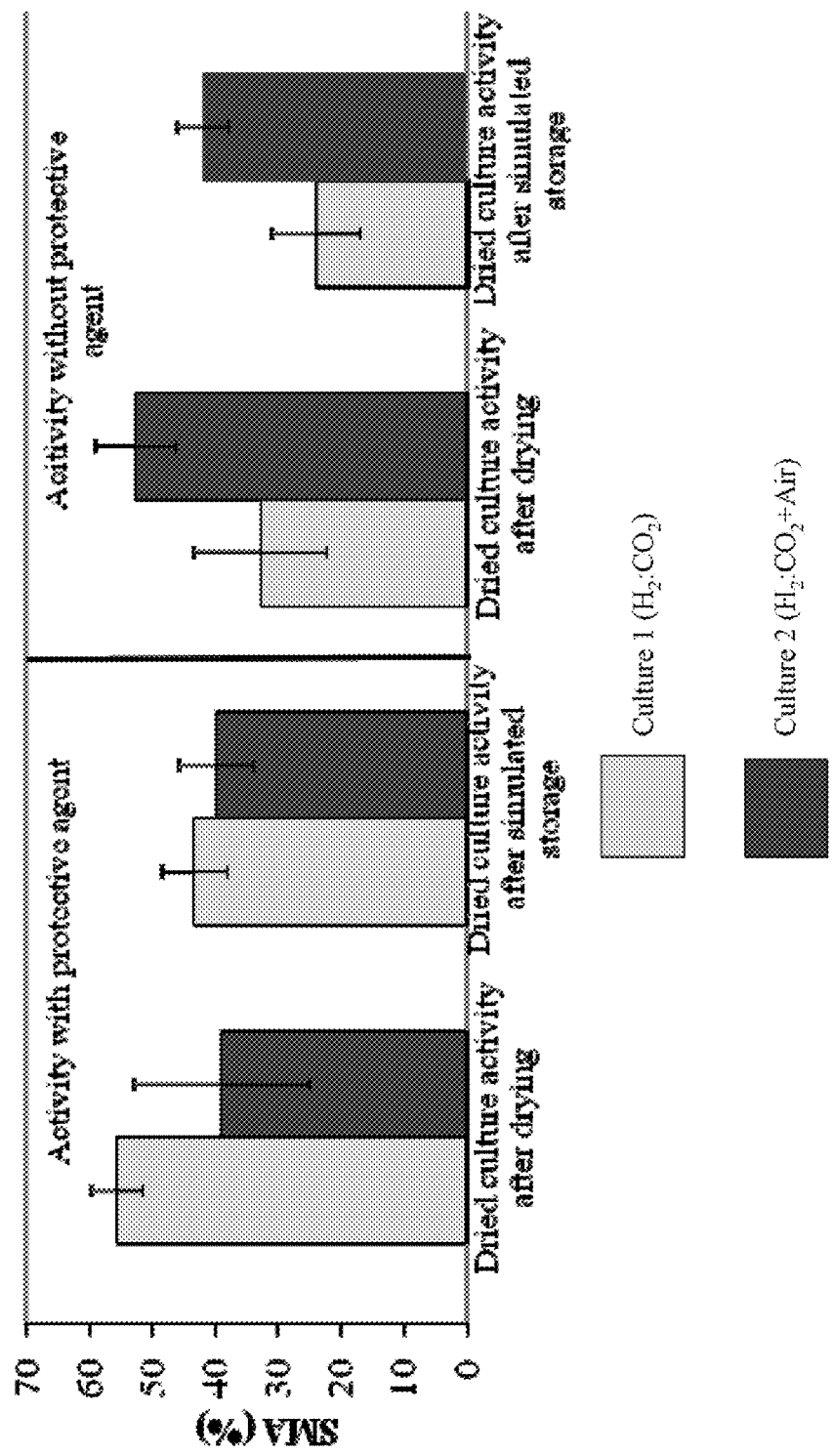
FIG. 8 illustrates percent activity of air-dried cultures with and without addition of cryoprotectant with respect to wet cultures. Error bars represent standard deviation among three replicates.

As indicated in FIGS. 6-8, the cultures retained 30 to 50% of their original methane production activity after air drying at the elevated temperature.

REFERENCES FOR EXAMPLE 2

APHA (American Public Health Association), AWWA (American Waterworks Association), and WEF (Water Environment Federation) (1998). *Standard Methods for the Examination of Water and Wastewater*, 20th edition.

Coates J. D., Coughlan M. F. and Colleran E. (1996). Simple method for the measurement of the hydrogenotrophic methanogenic activity of anaerobic sludges. *J Microbiol Methods*. 26(3), 237-246.

Colleran E., Concannon F., Golden T., Geoghegan F., Crumlish B., Killilea E., Henry M. and Coates J. (1992). Use of methanogenic activity tests to characterize anaerobic sludges, screen for anaerobic biodegradability and determine toxicity thresholds against individual anaerobic trophic groups and species. *Water Science & Technology [WATER SCI.TECHNOL.].* 25(7).

Sakane T., Kuroshima K. (1997). Viabilities of dried cultures of various bacteria after preservation for over 20 years and their prediction by the accelerated storage test. *Microbiol Cult. Coll.* 13, 1-7.

Schauer-Gimenez A. E., Zitomer D. H., Maki J. S, and Struble C. A. (2010). Bioaugmentation for Improved Recovery of Anaerobic Digesters After Toxicant Exposure. *Water Res.*

I claim:

1. A method for preserving methanogens, the method comprising drying a liquid culture comprising the methanogen in air to obtain a dried culture comprising the methanogens, wherein prior to the performing drying, the liquid culture was grown in the presence of oxygen, and wherein after the dried culture is reconstituted, the reconstituted culture retains a relatively high specific methanogenic activity against $H_2:CO_2$ after drying as compared to a reconstituted culture that was not grown in the presence of oxygen, and wherein the specific methanogenic activity against $H_2:CO_2$ is at least 30% of the specific methanogenic activity of the liquid culture against $H_2:CO_2$ prior to drying.

2. The method of claim 1, wherein drying comprises heating the liquid culture to a temperature of at least 80° C.

3. The method of claim 2, where the liquid culture is heated for at least 10 minutes.

4. The method of claim 2, wherein the liquid culture is subjected to a vacuum during the heating.

5. The method of claim 1, wherein drying comprises freeze-drying the liquid culture.

6. The method of claim 1, wherein the methanogens comprise hydrogenotrophic methanogens.

7. The method of claim 6, wherein the hydrogenotrophic methanogens belong to the order Methanomicrobiales or to the order Methanobacteriales.

8. The method of claim 7, wherein the hydrogenotrophic methanogens comprise *Methanospirilum hungatei*, or a related hydrogenotrophic methanogen.

9. The method of claim 8, wherein *Methanospirillum hungatei* or the related hydrogenotrophic methanogen represent at least 95% of hydrogenotrophic methanogens belonging to the order Methanomicrobiales in the culture.

10. The method of claim 6, wherein the hydrogenotrophic methanogens comprises *Methanobacterium beijingense, Methanolinea tarda*, or a related hydrogenotrophic methanogen.

11. The method of claim 1, wherein the methanogens comprise acetotrophic methanogens belonging to the order Methanosarcinales.

12. The method of claim 1, further comprising adding a cryoprotectant to the liquid culture prior to drying the liquid culture.

13. The method of claim 2, wherein the cryoprotectant is added at a concentration of at least 5 g/ml.

14. The method of claim 1, wherein the dried culture has a relative moisture content of less than 15% by mass.

15. The method of claim 1, wherein after the dried culture is reconstituted, the reconstituted cultures has a specific methanogenic activity against $H_2:CO_2$ that is at least 20 ml $CH_4$/hr-g of volatile suspended solids (VSS).

16. The method of claim 1, wherein prior to performing drying, the liquid culture was grown in the presence of an organic acid or a salt thereof.

* * * * *

SEQUENCE LISTING

```
<160> NUMBER OF SEQ ID NOS: 8

<210> SEQ ID NO 1
<211> LENGTH: 1466
<212> TYPE: DNA
<213> ORGANISM: Methanospirillum hungatei
<220> FEATURE:
<221> NAME/KEY: misc_feature
<222> LOCATION: (7)..(7)
<223> OTHER INFORMATION: n is a, c, g, or t

<400> SEQUENCE: 1
attctgnttg atcctgccag aggccactgc tatcggggtt tgactaagcc atgcgagtcg      60
agaggtgcaa gacctcggcg tactgctcag taacacgtgg acaatctgcc ctgaagagga    120
ggataatccc gggaaactgg gggtaatact ccatagttcg tgctgactgg aatgttatgc    180
gaacgaaaga tccgtcgctt caggatgagt ctgcggccga ttaggtagtt gttggggtaa    240
cggcccaaca agcctgtcat cggtacgggt tgtgggagca agagcccgga gatggattct    300
gagacacgaa tccaggccct acggggcgca gcaggcgcga aaactttacc atgcgggcaa    360
ccgtgataag gaaacccga gtgccagcac aggctggctg tccaccagtg taaataactg     420
gtgaagaaag ggccgggcaa gaccggtgcc agccgccgcg gtaataccgg cggctcgagt    480
ggtggccgct attactgggc ttaaagggtc cgtagctgga tatacaagtc ccttgagaaa    540
tccgccggct taaccggtgg gcgttcaggg gaaactgtat ttctagggac cgggagaggt    600
gagaggtact gccggggtag gagtgaaatc ctgtaatccc ggtgggacca cctatggcga    660
aggcatctca ccagaacggg tccgacagtg agggacgaaa gctggggag caaaccggat     720 tagatacccg ggtagtccca gctgtaaacg atgcgcgtta ggtgtgtcag tgaccacgtg    780
tcactgaggt gccgaaggga aaccgtgaaa cgcgccgcct ggggagtacg gtcgcaaggc    840
tgaaacttaa aggaattggc gggggagcac cacaacgggt ggagcctgcg gtttaatcgg    900
actcaacgcc ggaaatctca ccggataaga cagctgaatg atagtcggga tgaagactct    960
acttgactag ctgagaggag gtgcatggcc gtcgtcagtt cgtactgtga agcatcctgt   1020
ttagtcaggc aacgagcgag acccacgcga gcagttgcca gcttgacctt cgggttgatg   1080
gggacactgc tcggaccgcc tctgctaaag gggaggaag aatgggcaac ggtaggtcag    1140
catgccccga attatccggg ctacacgcgg gctacaatgg acaggacaat gggtttcgac    1200
accgagaggt gaggataatc tcctaaacct gtccgaagtt cggattgcgg gttgtaactc   1260
acccgcatga agctggaatc cgtagtaatc gcgtttcaac atagcgcggt gaatatgtcc   1320
ctgctccttg cacacaccgc ccgtcaaacc acccgagtga ggtcttgatg aggatgtatc    1380
attgatatgt tcgaatctgg gttttgcaag gggggttaag tcgtaacaag gtagccgtag    1440
gggaatctgc ggctggatca cctcct                                        1466

<210> SEQ ID NO 2
<211> LENGTH: 743
<212> TYPE: DNA
```

<213> ORGANISM: Methanospirillum hungatei

<400> SEQUENCE: 2

| | | | | | |
|---|---|---|---|---|---|
| cttcattacc | gcataccgca | tgtgtgccgg | agaagcagca | gtcgctgacc | tgtcctttgc | 60 |
| agcaaagcac | gctggtgtta | tccagatggc | aagtcacctc | ccggcccgtc | gtgcccgtgg | 120 |
| tccaaatgaa | ccaggaggta | tcatgttcgg | acactttgct | gacatgatcc | aggcaaaccg | 180 |
| gaagtacccg | aatgacccag | caaaggcatc | acttgaggtt | gtcggtgcag | gttgtatgct | 240 |
| cttcgaccag | atctggctcg | gttcctacat | gtctggtggt | gtcggattta | cccagtatgc | 300 |
| aaccgcagca | tacaccgaca | acatcctcga | tgagttcacc | tactatggta | tggactacat | 360 |
| caaggacaag | tacaaagtcg | actggaagaa | cccaagcccg | aaagacaagg | tcaagccaac | 420 |
| ccaggagatc | gtcaacgaca | ttgccggaga | ggtcaccctc | aatgcaatgg | agcagtacga | 480 |
| acagttccca | accatgatgg | aagaccactt | tggtggttcc | cagcgtgcag | gagttatcgc | 540 |
| agcagcatcc | ggtctgtctg | tcggtgtcgc | aacagcaaac | tccaacgcag | gtctgaacgg | 600 |
| atggtacctc | tccatgctca | tgcacaagga | aggctggtca | cgtctcggat | tcttcggata | 660 |
| cgacctgcag | gaccagtgtg | gttccaccaa | ctcactctct | gtcagacctg | acgagggttg | 720 |
| tatcggtgaa | taccgtggtc | cta | | | | 743 |

<210> SEQ ID NO 3
<211> LENGTH: 1433
<212> TYPE: DNA
<213> ORGANISM: Methanolinea tarda

<400> SEQUENCE: 3

| | | | | | |
|---|---|---|---|---|---|
| ttccggttga | tcctgccgga | ggccactgct | atcggggttc | gattaagcca | tgcgagtcga | 60 |
| gaggtgcaag | acctcggcgc | actgctcagt | aacacgtgga | taacctaccc | tcaggtgggg | 120 |
| gataaccccg | ggaaactggg | gataataccc | catagaccag | ggacgctgga | atgcccctg | 180 |
| atcgaaaggt | ccgccgcctg | aggatgggtc | tgcggccgat | taggttgttg | ttggggtaac | 240 |
| ggcccaacaa | gcctttgatc | ggtacggggt | gtgagagcaa | gagcccggag | atggattctg | 300 |
| agacacaaat | ccaggcccta | cggggcgcag | caggcgcgaa | aactttacaa | tgcgagaaat | 360 |
| cgtgataagg | gaaccccgag | tgcccgtaaa | ttcgggctgt | ccatcagcgt | aaaaaactgg | 420 |
| tgaagaaagg | gccgggcaag | accggtgcca | gccgccgcgg | taataccggc | ggctcgagtg | 480 |
| gtggccacta | ttactgggct | taaagcgtcc | gtagctggat | tgttaagtct | cttgggaaat | 540 |
| ccgccggctt | aaccggcggg | cgttcaggag | aaactgcaa | tctagggacc | gggagaggtg | 600 |
| agaggtactc | caggggtagg | agtgaaatcc | tgtaatcctt | gggggaccac | ctgtggcgaa | 660 |
| ggcgtctcac | tagaacggct | ccgacagtga | gggacgaaag | ctgggggagc | aaaccggatt | 720 |
| agatacccgg | gtagtcccag | ctgtaaacga | tgcgcgttag | gtgtatcggt | gaccacgagt | 780 |
| catcgaggtg | ccgaagggaa | accgtgaaac | gtgccgcctg | gaagtacgg | tcgcaaggct | 840 |
| gaaacttaaa | ggaattggcg | gggagcacc | acaacgggtg | gagcctgcgg | tttaattgga | 900 |
| ctcaacgccg | ggaagctcac | cggataagac | agctggatga | tagccgggct | gaagactctg | 960 |
| cttgactagc | tgagaggagg | tgcatggccg | tcgtcagttc | gtactgtgaa | gcatcctgtt | 1020 |
| aagtcaggca | acgagcgaga | cccacgccaa | cagttgccag | cgtatcctcc | gggatgacgg | 1080 |
| ggacactgtt | gggaccgcct | ctgctaaaga | ggaggaagga | atgggcaacg | gtaggtcagc | 1140 |
| atgccccgaa | ttatcgggc | tacacgcggg | ctacaatggt | caggacaatg | ggtatcgaca | 1200 |
| ccgagaggtg | aaggcaatct | cctaaacctg | atcgtagttc | ggattgtggg | ctgcaactcg | 1260 |

| | |
|---|---|
| cccacatgaa gctggaatcc gtagtaatcg cgtttcaaaa tagcgcggtg aatatgtccc | 1320 |
| tgctccttgc acacaccgcc cgtcaaacca cccgagtggg gtcttgatga ggctgcggtt | 1380 |
| gccgccgtgg tcgaatctag gttccgcaag gggggttaag tcgtaacaag gta | 1433 |

<210> SEQ ID NO 4
<211> LENGTH: 763
<212> TYPE: DNA
<213> ORGANISM: Methanolinea tarda

<400> SEQUENCE: 4

| | |
|---|---|
| gccatgcaga ttggtatgtc cttcatcggt gcctaccgca tgtgcgccgg tgaggcggcg | 60 |
| accgctgacc ttgcattcgc agcaaagcac gccggtgtca tccagatggg tgagatcctg | 120 |
| cctgcacgcc gtgccgtggg cccgaacgag cccgtggca tcaagttcgg acactttgcc | 180 |
| gacatggtcc agacggacag gaagtacccg aacgaccccg cacgcgcctc cctcgaggtc | 240 |
| gtgggtgcag gacgatgct cttttgaccag atctggctcg gtcctacat gtccggcggt | 300 |
| gtcgggttca cgcagtacgc aactgccgcc tacaccgaca acatcctcga tgactatacc | 360 |
| tactacggta tggactacat caagcagaaa tacaaagtcg actggcagaa cccgaacgag | 420 |
| aaggacaagg tcaagccgac ccaggacatc gtcaacgaca tcgcaacgga ggtcaccctc | 480 |
| tacggcatgg agcagtacga gcacttcccg actgcactcg aggaccactt cggcggttcc | 540 |
| cagcgtgcgt cggtccttgc tgctgcatcc ggtctcacga ccgcaattgc cacagggaac | 600 |
| tccaatgccg gactgaacgg ctggtacctg tccatgctcc tgcacaagga gggctggtca | 660 |
| cggctcggct tctacggata cgacctgcag gaccagtgcg gttccgcaaa caccgagtcc | 720 |
| atccgtgcag acgagggttg tgtcggagag ctccgcgggg cca | 763 |

<210> SEQ ID NO 5
<211> LENGTH: 1349
<212> TYPE: DNA
<213> ORGANISM: Methanobacterium beijingense

<400> SEQUENCE: 5

| | |
|---|---|
| ttccggttga tcctgccgga ggccactgct attggggtcc gattaagcca tgcaagtcga | 60 |
| acgttcttcg gaacgtggca acggctcag taacacgtgg ataacctacc cttaggaccg | 120 |
| ggataaccct gggaaactgg ggataatacc ggatatatgg agatacctgg aatggttctc | 180 |
| cacttaaagc tccggcgcct aaggatggat ctgcggcaga ttaggtcgtt ggtggggtaa | 240 |
| tggcccacca agcctttgat ctgtacgggt tgtgagagca agagcccgga gatgaacct | 300 |
| gagacaaggt tccaggccct acggggcgca gcaggcgcga aacctccgca atgcgagcaa | 360 |
| tcgcgacggg ggaccccaa gtgccactct aacggggtg gcttttctta agtgtaaaaa | 420 |
| gcttttggaa taagggctgg gcaagaccgg tgccagccgc cgcggtaaca ccggcagccc | 480 |
| aagtggtggc cattttttatt gggcctaaag cgttcgtagc cggcctgata agtctctggt | 540 |
| gaaatcccgc agcttaactg tgggaattgc tggagatact atcaggcttg aggtcgggag | 600 |
| aggttagagg tactcccagg gtaggggtga aatcctataa tcctgggagg accacctgtg | 660 |
| gcgaaggcgt ctaactggaa cgaacctgac ggtgagtaac gaaagccagg ggcgcgaacc | 720 |
| ggattagata cccgggtagt cctggccgta acgatgtgg acttggtgtt gggatggcct | 780 |
| cgagctgccc cagtgccgaa gggaagctgt taagtccacc gcctgggaag tacggtcgca | 840 |
| agactgaaac ttaaaggaat tggcggggga gcaccacaac gcgtggagcc tgcggtttaa | 900 |
| atggattcaa cgccggacat ctcaccaggg gcgacagcag gatgatggcc agattgacga | 960 |

-continued

```
tcttgcttga caagctgaga ggaggtgcat ggccgccgtc agctcgtacc gtgaggcgtc   1020
ctgttaagtc aggcaacgag cgagacccac gcccttagtt accagcggat ccttacagga   1080
tgccgggcac actaagggga ccgccagtga taaactggag gaaggagtgg acgacggtag   1140
gtccgtatgc cccgaatccc ctgggctaca cgcgggctac aatggctagg acaatgggtt   1200
ccaacactga aaagtgaagg taatctccta aacctagtct tagttcggat tgagggctgt   1260
aactcgccct catgaagctg gaatgcgtag taatcgcgtg tcataatcgc gcggtgaata   1320
cgtccctgct ccttgcacac accgcccgt                                     1349

<210> SEQ ID NO 6
<211> LENGTH: 493
<212> TYPE: DNA
<213> ORGANISM: Methanobacterium beijingense

<400> SEQUENCE: 6
atgatcagat ttggctaggt tcatacatgt ctggcggtgt aggattcacc cagtacgcaa     60
ccgcagcata caccgacaac atactggacg acttcaccta ctttggtaaa gagtacgtag    120
aagacaaata cggtataacc gaagcaccta acaccatgga caccgttctg gatgttgctt    180
cagaagtcac tttctacgga ctggaacagt acgaagaata cccatcacta cttgaagatc    240
agttcggagg atcacagaga gcagcagtaa ccgctgcagc atctgcatgt tccactggat    300
ttgcaactgg aaacgcccaa actgctttaa gtggatggta tctctctatg tacctgcaca    360
aagaacagca cagccgactt ggattctacg gttacgacct tcaggaccag tgtggtgcat    420
ctaacgtatt ctcaattaga ggagatgaag gattaccact ggaattgaga ggagctaact    480
atccaaacta cgc                                                       493

<210> SEQ ID NO 7
<211> LENGTH: 20
<212> TYPE: DNA
<213> ORGANISM: Artificial
<220> FEATURE:
<223> OTHER INFORMATION: Forward primer for amplifying 16S rRNA gene of
      Archaeal communities

<400> SEQUENCE: 7
ttccggttga tccygccgga                                                 20

<210> SEQ ID NO 8
<211> LENGTH: 19
<212> TYPE: DNA
<213> ORGANISM: Artificial
<220> FEATURE:
<223> OTHER INFORMATION: Reverse primer for amplifying 16S rRNA gene of
      Archael communities

<400> SEQUENCE: 8
yccggcgttg amtccaatt                                                  19
```